United States Patent [19]

Fory et al.

[11] 4,443,243
[45] Apr. 17, 1984

[54] N-PHENYLSULFONYL-N-TRIAZINYLUREAS

[75] Inventors: Werner Fory, Basel; Karl Gass, Magden; Willy Meyer, Riehen; Rolf Schurter, Binningen, all of Switzerland

[73] Assignee: Ciba-Geigy Corporation, Ardsley, N.Y.

[21] Appl. No.: 396,959

[22] Filed: Jul. 9, 1982

[30] Foreign Application Priority Data

Jul. 16, 1981 [CH] Switzerland ............ 4667/81

[51] Int. Cl.³ ............ C07D 251/44; C07D 251/46; C07D 251/42; A01N 43/66
[52] U.S. Cl. ............ 71/93; 544/211
[58] Field of Search ............ 71/93; 544/211

[56] References Cited

U.S. PATENT DOCUMENTS

| 4,127,405 | 11/1978 | Levitt | 544/211 |
| 4,190,432 | 2/1980 | Levitt | 544/211 |
| 4,371,391 | 2/1983 | Levitt | 544/211 |

FOREIGN PATENT DOCUMENTS

| 1514 | 4/1979 | European Pat. Off. |
| 1415 | 4/1979 | European Pat. Off. |
| 23422 | 2/1981 | European Pat. Off. |
| 2715786 | 10/1977 | Fed. Rep. of Germany |
| 1468747 | 1/1967 | France |

OTHER PUBLICATIONS

Adams et al., Chemical Abstracts, vol. 96, entry 69044s (1982).

Primary Examiner—John M. Ford
Attorney, Agent, or Firm—Frederick H. Rabin

[57] ABSTRACT

N-Phenylsulfonyl-N'-pyrimidinyl- and -triazinylureas of the general formula

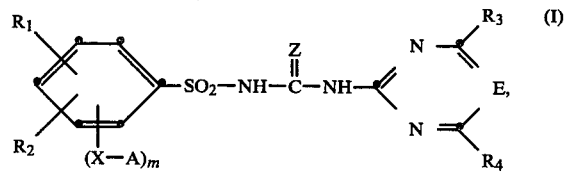

and the salts of these compounds with amines, with alkali or alkaline-earth metal bases or with quaternary ammonium bases, have good pre- and post-emergence selective, herbicidal and growth-regulating properties.

The symbols in this formula are as follows:

A is a $C_3$–$C_6$-alkynyl group,
E is the methine group or nitrogen,
X is oxygen, sulfur or a sulfinyl or sulfonyl bridge,
Z is oxygen or sulfur,
m is the number one or two,
$R_1$ is hydrogen, halogen, $C_1$–$C_5$-alkyl or $C_2$–$C_5$-alkenyl or a group —Y—$R_5$,
$R_2$ is hydrogen, halogen, $C_1$–$C_5$-alkyl, $C_2$–$C_5$-alkenyl or $C_1$–$C_4$-haloalkyl, or a group —Y—$R_5$, —$COOR_6$, —$NO_2$ or —CO—$NR_7$—$R_8$,
$R_3$ and $R_4$ independently of one another are each hydrogen, $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy, halogen or alkoxyalkyl having at most 4 carbon atoms,
$R_5$ and $R_6$ are each $C_1$–$C_5$-alkyl, $C_2$–$C_5$-alkenyl or $C_2$–$C_6$-alkynyl,
$R_7$ and $R_8$ independently of one another are each hydrogen, $C_1$–$C_5$-alkyl, $C_2$–$C_5$-alkenyl or $C_2$–$C_6$-alkynyl, and
Y is oxygen, sulfur or a sulfinyl or sulfonyl bridge.

21 Claims, No Drawings

N-PHENYLSULFONYL-N-TRIAZINYLUREAS

The present invention relates to novel N-phenylsulfonyl-N'-pyrimidinyl- and -triazinylureas which have a herbicidal action and an action regulating plant growth, to processes for producing them, to compositions containing them as active ingredients, and also to the use thereof for combating weeds, particularly selectively in cultivated crops, or for regulating and reducing plant growth. The invention relates in addition to novel phenylsulfonamides and N-phenylsulfonylcarbamates produced as intermediates.

The N-phenylsulfonyl-N'-pyrimidinyl- and -triazinylureas according to the invention correspond to the general formula I

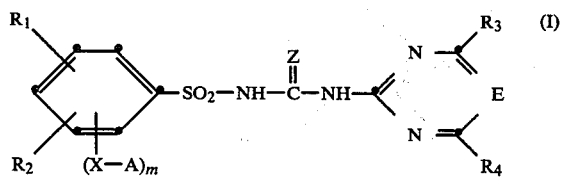

wherein
A is a $C_3$–$C_6$-alkynyl group,
E is the methine group or nitrogen,
X is oxygen, sulfur or a sulfinyl or sulfonyl bridge,
Z is oxygen or sulfur,
m is the number one or two,
$R_1$ is hydrogen, halogen, $C_1$–$C_5$-alkyl or $C_2$–$C_5$-alkenyl or a group —Y—$R_5$,
$R_2$ is hydrogen, halogen, $C_1$–$C_5$-alkyl, $C_2$–$C_5$-alkenyl or $C_1$–$C_4$-haloalkyl, or a group —Y—$R_5$, —COO$R_6$, —NO$_2$ or —CO—NR$_7$-$R_8$,
$R_3$ and $R_4$ independently of one another are hydrogen, $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy, halogen or alkoxyalkyl having at most 4 carbon atoms,
$R_5$ and $R_6$ are each $C_1$–$C_5$-alkyl, $C_2$–$C_5$-alkenyl or $C_2$–$C_6$-alkynyl,
$R_7$ and $R_8$ independently of one another are each hydrogen, $C_1$–$C_5$-alkyl, $C_2$–$C_5$-alkenyl or $C_2$–$C_6$-alkynyl, and
Y is oxygen, sulfur or a sulfinyl or sulfonyl bridge; and the invention relates also to the salts of these compounds.

Urea compounds, triazine compounds and pyridimine compounds having herbicidal activity are known in general. There have recently been described arylsulfamoyl-heterocyclyl-aminocarbamoyl compounds having a herbicidal action and an action regulating plant growth, for example in the European Patent Publications Nos. 1514 and 1515, in the U.S. Pat. No. 4,127,405, and German Offenlegungsschrift No. 2,715,786 and the French Patent Specification No. 1,468,747.

Alkyl in the definitions is straight-chain or branched-chain alkyl, for example methyl, ethyl, n-propyl, i-propyl, the four isomeric butyl groups, n-amyl, i-amyl, 2-amyl, 3-amyl, n-hexyl or i-hexyl.

By alkoxy is meant: methoxy, ethoxy, n-propyloxy, i-propyloxy and the four isomeric butyloxy groups, in particular however methoxy, ethoxy or i-propoxy.

Examples of alkylthio are: methylthio, ethylthio, n-propylthio, i-propylthio and n-butylthio, but especially methylthio and ethylthio.

Examples of alkenyl groups are: vinyl, allyl, isopropenyl, 1-propenyl, 1-butenyl, 2-butenyl, 3-butenyl, 1-isobutenyl, 2-isobutenyl, 1-pentenyl, 2-pentenyl, 3-pentenyl and 4-pentenyl, particularly however, vinyl, allyl and 4-pentenyl.

Examples of alkylsulfinyl are: methylsulfinyl, ethylsulfinyl, n-propylsulfinyl and n-butylsulfinyl, especially methylsulfinyl and ethylsulfinyl.

Examples of alkylsulfonyl are: methylsulfonyl, ethylsulfonyl, n-propylsulfonyl and n-butylsulfonyl, particularly however methylsulfonyl and ethylsulfonyl.

Halogen in the definitions, as well as in haloalkyl, -alkoxy, -alkylsulfinyl, -alkylsulfonyl and -alkylthio, is fluorine, chlorine and bromine, preferably fluorine and chlorine.

Alkynyl groups in the definitions of the above symbols are as a rule: propargyl, 2-butynyl and 3-butynyl, as well as isomeric pentynyl or hexynyl groups; the alkynyl group is preferably however propargyl or 2- or 3-butynyl.

The invention embraces also the salts which the compounds of the formula I can form with amines, alkali metal bases and alkaline-earth metal bases or quaternary ammonium bases. To be emphasised among the alkali metal and alkaline-earth metal hydroxides as salt formers are the hydroxides of lithium, sodium, potassium, magnesium or calcium, especially however of sodium or potassium. Examples of amines suitable for forming salts are: primary, secondary and tertiary aliphatic and aromatic amines, such as methylamine, ethylamine, propylamine, i-propylamine, the four isomeric butylamines, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and i-quinoline, in particular however ethyl-, propyl-, diethyl- or triethylamine, but especially isopropylamine and diethanolamine. Examples of quaternary ammonium bases are in general the cations of haloammonium salts, for example the tetramethylammonium cation, the trimethylbenzylammonium cation, the triethylbenzylammonium cation, the tetraethylammonium cation or the trimethylethylammonium cation, but also the ammonium cation.

Preferred compounds of the formula I are those in which:
 (a) Z is oxygen, and
 (b) $R_3$ and $R_4$ together contain no more than 4 carbon atoms.

The group (a) can be divided into two further subgroups consisting of compounds in which
 (aa) m is the number one, and
 (ab) m is the number two.

Preferred compounds from the group (aa) are those in which the group —X—A is in the 2- or 3-position with respect to the sulfonyl group. Compounds particularly preferred in this group are those wherein the group —X—A is in the 2-position.

A preferred group from the group (ab) is formed by the compounds in which the two —X—A groups are in the 2- and 5-positions with respect to the sulfonyl group.

A further preference with regard to compounds of the aforementioned subgroups of the groups (aa) and (ab) is that $R_3$ and $R_4$ together contain at most 4 carbon atoms. There are thus formed the especially preferred groups of compounds of the formula I wherein:
 (aab) only one —X—A group is present in the 2-position with respect to the sulfonyl group, Z is oxygen, and $R_3$ and $R_4$ together contain no more than 4 carbon atoms atoms, and (abb) two —X—A groups are present in the 2- and 5-position with respect to the sulfonyl group, Z is oxygen, and $R_3$ and $R_4$ together contain no more than 4 carbon atoms.

Preferred compounds from the group (aab) are those in which $R_1$ is hydrogen, and $R_2$ is in the 5- or 6-position with respect to the sulfonyl group. And of these compounds moreover, those are preferred in which $R_2$ is hydrogen, halogen, $C_1$–$C_4$-alkoxy, nitro or $COOR_6$.

A further preference within the last-mentioned group is for the compounds in which $R_2$ is hydrogen, fluorine, nitro or $C_1$–$C_4$-alkoxy, and $R_3$ and $R_4$ are each hydrogen, $C_1$–$C_4$-alkyl, $C_1$–$C_4$-alkoxy, $C_1$–$C_4$-alkylthio, $C_1$–$C_3$-haloalkoxy, halogen or alkoxyalkyl, where $R_3$ and $R_4$ together contain no more than 4 carbon atoms.

Compounds among these which are in their turn preferred are those in which $R_2$ is hydrogen, and $R_3$ and $R_4$ are each $C_1$–$C_4$-alkyl, $C_1$–$C_4$-alkoxy, methylthio, 2,2,2-trifluoroethoxy, difluoromethoxy, 1,1,2,2-tetrafluoroethoxy, halogen or alkoxyalkyl. A further preference within the last-mentioned group is for the compounds in which X is oxygen or sulfur. More especially preferred of these, however, are the compounds in which X is oxygen. Preferred compounds within this group are those in which A is propargyl.

Of the compounds of the formula I wherein Z is sulfur, those are preferred in which X is oxygen or sulfur, $R_3$ and $R_4$ independently of one another are each $C_1$–$C_3$-alkyl, $C_1$–$C_3$-alkoxy, $C_1$–$C_3$-alkylthio, difluoromethoxy or 2,2,2-trifluoroethoxy, with together at most 4 carbon atoms, and A is —CH$_2$—C≡CH, —CH$_2$—C≡C—CH$_3$ or —CH$_2$—CH$_2$—C≡CH, and the —X—A group occupies the 2-position, and m is the number 1.

The following are given as preferred individual compounds:
N-(2-propargyloxyphenyl-sulfonyl)-N'-(4-methoxy-6-methyl-1,3,5-triazin-2-yl)-urea,
N-(2-propargyloxyphenyl-sulfonyl)-N'-(4-ethyl-6-methoxy-1,3,5-triazin-2-yl)-urea,
N-(2-propargyloxyphenyl-sulfonyl)-N'-(4,6-dimethoxy-1,3,5-triazin-2-yl)-urea, and
N-(2-propargyloxyphenyl-sulfonyl)-N'-(4-ethoxy-6-methyl-1,3,5-triazin-2-yl)-urea.

The compounds of the formula I are produced in an inert organic solvent.

One process for producing the compounds of the formula I comprises reacting a phenylsulfonamide of the formula II

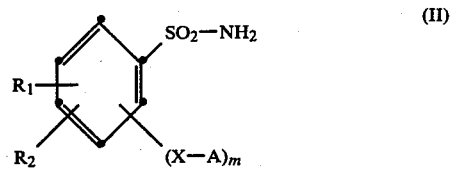
(II)

wherein A, $R_1$, $R_2$, X and m have the meanings defined under the formula I, in the presence of a base, with an N-pyrimidinyl- or -triazinylcarbamate of the formula III

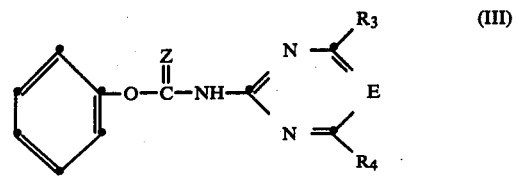
(III)

wherein E, $R_3$, $R_4$ and Z have the meanings defined under the formula I.

Compounds of the formula I are obtained, using a second process, by reacting a phenylsulfonylisocyanate or -isothiocyanate of the formula IV

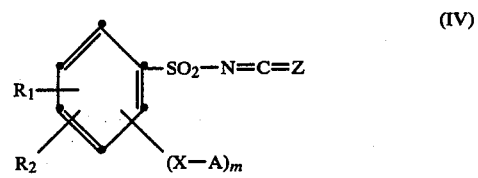
(IV)

wherein A, $R_1$, $R_2$, m, X and Z are as defined under the formula I, optically in the presence of a base, with an amine of the formula V

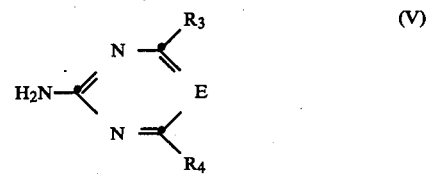
(V)

wherein E, $R_3$ and $R_4$ have the meanings defined under the formula I.

Compounds of the formula I are produced in a further process by reacting a sulfonamide of the formula II given above, optionally in the presence of a base, with an isocyanate or isothiocyanate of the formula VI

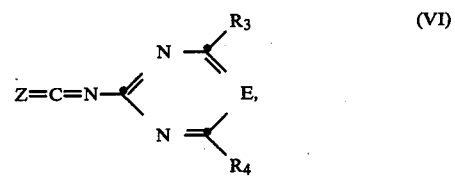
(VI)

wherein E, $R_3$, $R_4$ and Z are as defined under the formula I.

Finally, the compounds of the formula I can be obtained also by reacting an N-phenylsulfonylcarbamate of the formula VII

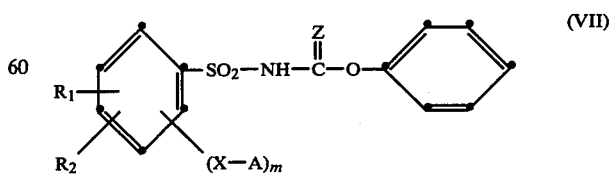
(VII)

wherein A, $R_1$, $R_2$, m, X and Z have the meanings defined under the formula I, with an amine of the above formula V.

The resulting ureas of the formula I can if desired be converted, by means of amines, alkali metal or alkaline-earth metal hydroxides or quaternary ammonium bases, into addition salts. This is effected for example by reaction with the equimolar amount of a base, and removal of the solvent by evaporation.

The starting materials of the formulae II, IV and VII are novel and can be produced by the following methods.

The novel sulfonamides of the formula II which are used as intermediates are obtained from the corresponding anilines by diazotisation and exchange of the diazo group for sulfur dioxide in the presence of a catalyst, such as copper-I chloride, in hydrochloric acid or acetic acid, and reaction of the formed phenylsulfonyl chloride with ammonia.

The compounds of the formula I can be obtained also by oxygen- or sulfur-alkynylation of hydroxy- or thio-phenylsulfonamides with the corresponding halides or sulfuric acid esters, or by reaction of ortho-halophenyl-sulfonamides with metal alcoholates or mercaptides, and optionally by oxidation thereof with for example periodates or peroxy acids to the corresponding sulfoxides and sulfones.

Ortho-substituted hydroxyphenyl- or substituted ortho-hydroxyphenylsulfonamides of the formula VIII

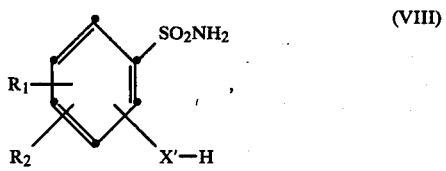

(VIII)

wherein $R_1$ and $R_2$ have the meanings defined under the formula I, and $X'$ is oxygen or sulfur, are known, as starting products of certain sulfonamide representatives of the formula II, from the Swiss Patent Application No. 3991/81-4. They can be obtained by ether cleavage of the corresponding $C_1$-$C_4$-alkoxyphenylsulfonamides for example with boron trihalides (reactions of this type are described in the U.S. Pat. No. 3,904,680 and in J. Am. Chem. Soc. 64, 1128 (1942), or by hydrogenolysis of the corresponding benzyloxyphenylsulfonamides, as described in J. Chem. Soc. 1958, 2903.

The alkoxyphenylsulfonamides for their part can be obtained from the corresponding alkoxyanilides, as already mentioned, or by chlorosulfonylation of alkoxybenzenes by reaction of the resulting phenylsulfonyl chlorides with ammonia. Such reactions have become known from J. Am. Chem. Soc. 62, 603 (1940).

The compounds of the formula II and VII used as intermediates are novel and were developed specifically for the synthesis of compounds of the formula I. These intermediates form further subject matter of the present invention.

The phenylsulfonylisocyanates of the formula IV can be obtained by reaction of the sulfonamides of the formula II with phosgene in the presence of butylisocyanate, in a chlorinated hydrocarbon as solvent, at reflux temperature. Similar production methods are described in "Neuere Methoden der präparativen organischen Chemie", Vol. VI, 211–229, Verlag Chemie, Weinheim, 1970.

The isothiocyanates of the formula IV are obtained by treatment of the sulfonamides of the formula II with carbon disulfide and potassium hydroxide, and subsequent reaction of the dipotassium salt with phosgene. Processes of this kind are described in Arch. Pharm. 299, 174 (1966).

The N-phenylsulfonylcarbamates of the formula VII are obtained by reaction of the sulfonamides of the formula II with diphenylcarbonate in the presence of a base. Similar processes are mentioned in the Japanese Patent Specification No. 61 169.

The starting materials of the formulae III, V and VI are in part known. New compounds of the formulae III and VI can be obtained, by known methods, from corresponding compounds of the formula V.

New fluoroalkoxy-aminopyrimidines and -triazines of the formula V and the production thereof, and also the production therefrom of corresponding compounds of the formulae III and VI, are described in the Swiss Patent Application No. 3527/82-8.

Isocyanates of the formula VI can be produced by reaction of amines of the formula V with oxalyl chloride in chlorinated hydrocarbons as solvents. Amines of the formula V are known and some are obtainable commercially, or they can be produced by known methods (cp. "The Chemistry of Heterocyclic Compounds", Vol. XIV, Interscience Publishers, New York, London.

These reactions to give compounds of the formula I are advantageously performed in aprotic, inert, organic solvents, such as methylene chloride, tetrahydrofuran, acetonitrile, dioxane and toluene.

The reaction temperatures are preferably between $-20°$ and $+120°$ C. The reactions proceed in general slightly exothermically, and can be carried out at room temperature. For the purpose of shortening the reaction time or for initiating the reaction, it is advantageous to apply heat for a short time up to the boiling point of the reaction mixture. The reaction times can be shortened also by the addition of some drops of a base or of isocyanate as a reaction catalyst.

The final products can be isolated by concentration by evaporation and/or by removal of the solvent by evaporation, and purified by recrystallisation or trituration of the solid residue in solvents in which they do not readily dissolve, such as ether, aromatic hydrocarbons or chlorinated hydrocarbons.

The active substances of the formula I are stable compounds, and the handling of them necessitates no special precautions being taken.

In smaller applied amounts, the compounds of the formula I are characterised by good selective growth-inhibiting and selective herbicidal properties, which render them excellently suitable for use in crops of useful plants, especially in crops of cereals, cotton, soya-bean, maize and rice. The preferred crops are cereals, such as wheat, barley and rye. Also destroyed in some cases are weeds which hitherto could be dealt with only by the use of total herbicides.

The mode of action of these active substances is unusual. Many are capable of being translocated, that is to say, they are taken up by the plant and transported to other locations, where they produce the desired effect. It is thus possible for example by surface treatment of perennial weeds to destroy them at their roots. The novel compounds of the formula I are effective in applied amounts which are very small compared with the amounts required to obtain the same effect using other herbicides and plant-growth regulators.

The compounds of the formula I also have excellent properties for regulating, especially reducing, plant growth. Both monocotyledons and dicotyledons are impaired in their growth. A reduction of the vegetative growth enables in the case of many cultivated plants the crop density to be raised, so that higher yields for the same area of land can be achieved.

An additional factor contributing to the increase in yield with the use of growth inhibitors is that the formation of blossom and fruit benefits to a greater extent from the nutritive substances, because the vegetative growth is restricted.

Thus, for example, the leguminosae frequently planted as cover crops in agriculture in tropical regions are selectively inhibited in their growth by the compounds of the formula I, the result being that soil erosion between the cultivated plants is prevented, without the cover crops being able to compete with the main cultivated crop.

Furthermore, the compounds of the formula I are suitable for preventing the sprouting of stored potatoes. Shoots frequently form on potatoes being stored during the winter, and the shoots cause shrinkage, loss in weight and rotting.

With larger applied amounts of active substance, all the tested plants were impaired in their development to the extent that they died.

The invention relates also to herbicidal and plant-growth-regulating compositions containing a novel active ingredient of the formula I, and also to processes for the pre- and post-emergence combating of weeds, and for the reduction of growth of monocotyledonous and dicotyledonous plants, particularly that of grasses, tropical cover crops and side shoots of tobacco plants.

The compounds of the formula I are used either in an unmodified form or preferably in compositions, together with auxiliaries customarily employed in formulation practice, and are thus processed, in a known manner, for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objects to be achieved and the given conditions.

The formulations, that is to say, the compositions or preparations containing the active ingredient of the formula I and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones, such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$-$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8-22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications: "Mc Cutcheon's Detergents and Emulsifiers Annual" MC Publishing Corp., Ridgewood, N.J., 1979; and Sisley and Wood, "Encyclopedia of Surface Active Agents", Chemical Publishing Co., Inc. New York, 1964.

The agrochemical preparations contain as a rule 0.1 to 95%, especially 0.1 to 80%, of active ingredient of the formula I, 1 to 99.9% of a solid or liquid additive, and 0 to 25%, particularly 0.1 to 25%, of a tenside.

Preferred formulations are made up in particular as follows (%=percent by weight):

| Emulsifiable concentrates | | |
|---|---|---|
| active ingredient: | 1 to 20%, | preferably 5 to 10% |
| surface active agent: | 5 to 30%, | preferably 10 to 20% |
| liquid carrier: | 50 to 94%, | preferably 70 to 85%. |
| Dusts | | |
| active ingredient: | 0.1 to 10%, | preferably 0.1 to 1% |
| solid carrier: | 99.9 to 90% | preferably 99.9 to 99%. |
| Suspension concentrates | | |
| active ingredient: | 5 to 75%, | preferably 10 to 50% |
| water | 94 to 25%, | preferably 90 to 30% |
| surface-active agent: | 1 to 40%, | preferably 2 to 30%. |
| Wettable powders | | |
| active ingredient: | 0.5 to 90%, | preferably 1 to 80% |
| surface-active agent: | 0.5 to 20%, | preferably 1 to 15% |
| solid carrier: | 5 to 95%, | preferably 15 to 90%. |
| Granulates | | |
| active ingredient: | 0.5 to 30%, | preferably 3 to 15% |
| solid carrier: | 99.5 to 70%, | preferably 97 to 85%. |

Whereas commercial products are preferably in the form of concentrated compositions, the compositions employed by the end-user are as a rule diluted. The preparations can for application be diluted down to 0.001% of active ingredient. The applied amounts are usually 0.01 to 10 kg, preferably 0.025 to 5, kg of active substance per hectare.

The compositions can also contain additives such as stabilisers, antifoaming agents, viscosity regulators, binders and adhesives, as well as fertilisers or other active substances for obtaining special effects.

In the following Examples, the temperatures are given in degrees Centigrade (°C.), and pressures in millibars (mb).

PRODUCTION EXAMPLES

EXAMPLE 1

(a) 2-Propargyloxyphenylsulfonamide

A mixture of 35 g of 2-hydroxyphenylsulfonamide, 55.2 g of potassium carbonate, 15.5 ml of propargyl bromide and 1000 ml of ethyl methyl ketone is refluxed for 1.5 hours; it is then cooled, filtered, and concentrated by evaporation. The yield after recrystallisation of the residue from ethyl acetate is 30 g of 2-propargyloxyphenylsulfonamide, m.p. 143°-145° C.

(b) N-(2-Propargyloxyphenylsulfonyl)-phenyl carbamate

A solution of 15.1 g of 2-propargyloxyphenylsulfonamide in 100 ml of diethylformamide is added dropwise within 10 minutes, at a maximum temperature of 10° C. in a nitrogen atmosphere, to the suspension of 3.09 g of 55% sodium hydride in 30 ml of absolute dimethylformamide. The reaction mixture is stirred for 15 minutes at room temperature; there is subsequently added dropwise, in the course of 20 minutes, a solution of 15.94 g of diphenyl carbonate in 100 ml of dimethylformamide, and the mixture is stirred for a further 45 minutes. The reaction mixture is afterwards taken up in a mixture of 600 g of ice, 90.5 ml of 2 N hydrochloric acid and 600 ml of ethyl acetate. The organic phase is washed twice with ice water, dried over sodium sulfate and concentrated by evaporation. Ether/petroleum ether (1:1) is added to the oily residue to thus obtain 21.4 g of crystalline N-(2-propargyloxyphenylsulfonyl)-phenyl carbamate, m.p. 155°-157° C.

(c) N-(2-Propargyloxyphenylsulfonyl)-N'-(4-methoxy-6-methyl-1,3,5-triazin-2-yl)-urea A mixture of 3.33 g of N-(2-propargyloxyphenylsulfonyl)-phenyl carbamate and 1.4 g of 2-amino-4-methoxy-6-methyl-1,3,5-triazine in 30 ml of absolute dioxane is refluxed for 45 minutes; the mixture is then cooled to room temperature, filtered, and concentrated by evaporation. The yield after trituration of the residue with 40 ml of ether is 2.38 g of crystalline N-(2-propargyloxyphenylsulfonyl)-N'-(4-methoxy-6-methyl-1,3,5-triazin-2-yl)-urea, m.p. 157°-158° C.

EXAMPLE 2

(a) 5-Methyl-2-propargyloxyphenylsulfonamide

A mixture of 24.3 g of 2-hydroxy-5-methylphenylsulfonamide, 36.0 g of potassium carbonate, 16.7 g of propargyl bromide and 500 ml of acetonitrile is stirred at 50° C. for 4.5 hours. The reaction mixture is then filtered, and concentrated by evaporation. The yield after recrystallisation from ethyl acetate is 23.9 g of 5-methyl-2-propargyloxyphenylsulfonamide, m.p. 169°-170° C.

(b) 5-Methyl-2-propargyloxyphenylsulfonylisocyanate

A mixture of 22.4 g of 5-methyl-2-propargyloxyphenylsulfonamide, 9.9 g of n-butylisocyanate, 0.3 g of 1,4-diazabicyclo(2,2,2)octane and 350 ml of absolute xylene is refluxed for 30 minutes; and about 20 g of phosgene are subsequently introduced at 115°-120° C. during 2 hours. After the excess of phosgene has been removed from the reaction mixture by feeding in nitrogen, the mixture is cooled to room temperature, filtered, and concentrated in vacuo. There is thus obtained as crude product 28.1 g of 5-methyl-2-propargyloxyphenylsulfonylisocyanate in the form of brown oil. This crude product is used, without further purification, in the subsequent stage.

(c) N-(5-Methyl-2-propargyloxyphenylsulfonyl)-N'-(4-chloro-6-methoxypyrimidin-2-yl)-urea A solution of 9.4 g of crude 5-methyl-2-propargyloxyphenylsulfonylisocyanate in 50 ml of absolute tetrahydrofuran is added dropwise at room temperature, within 10 minutes, to a solution of 3.7 g of 2-amino-4-chloro-6-methoxy-pyrimidine and 0.1 g of 1,4-diazadicyclo[2.2.2]octane in 60 ml of absolute tetrahydrofuran, in the course of which the temperature rises slightly. The reaction solution is stirred for 18 hours at room temperature; it is then filtered, and concentrated by evaporation. The residue is crystallised from ethyl acetate to thus obtain 5.8 g of N-(5-methyl-2-propargyloxyphenylsulfonyl)-N'-(4-chloro-6-methoxy-pyrimidin-2-yl)-urea, m.p. 202°–204° C.

The intermediate and final products listed in the following Tables are obtained in an analogous manner.

TABLE 1

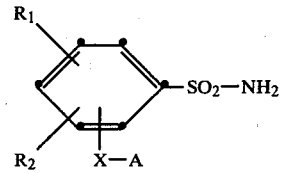

| $R_1$ | $R_2$ | X | A | Position of X-A | Physical data |
|---|---|---|---|---|---|
| H | H | O | $-CH_2-C\equiv CH$ | 2 | m.p. 143–145° |
| H | H | S | $-CH_2-C\equiv CH$ | 2 | |
| H | H | O | $-CH_2-CH_2-C\equiv CH$ | 2 | |
| H | H | O | $-CH_2-C\equiv C-CH_3$ | 2 | |
| 6-Cl | H | O | $-CH_2-C\equiv CH$ | 2 | |
| 6-Cl | H | O | $-CH_2-C\equiv C-CH_3$ | 2 | |
| 6-Cl | H | O | $-CH_2-CH_2-C\equiv CH$ | 2 | |
| 6-OCH$_3$ | H | O | $-CH_2-C\equiv CH$ | 2 | |
| 6-OCH$_3$ | H | O | $-CH_2-C\equiv C-CH_3$ | 2 | |
| 6-CH$_3$ | H | O | $-CH_2-C\equiv CH$ | 2 | |
| 6-CH$_3$ | H | O | $-CH_2-CH_2-C\equiv CH$ | 2 | |
| 6-NO$_2$ | H | O | $-CH_2-C\equiv CH$ | 2 | |
| 6-NO$_2$ | H | O | $-CH_2-C\equiv C-CH_3$ | 2 | |
| 6-COOCH$_3$ | H | O | $-CH_2-C\equiv CH$ | 2 | |
| 5-Cl | H | O | $-CH_2-C\equiv CH$ | 2 | m.p. 145° |
| 5-Cl | H | O | $-CH_2-CH_2-C\equiv CH$ | 2 | |
| 5-Cl | H | O | $-CH_2-C\equiv C-CH_3$ | 2 | |
| 5-Br | H | O | $-CH_2-C\equiv CH$ | 2 | |
| 5-Br | H | O | $-CH_2-C\equiv C-CH_3$ | 2 | |
| 5-Br | H | O | $-CH_2-CH_2-C\equiv CH$ | 2 | |
| 5-F | H | O | $-CH_2-C\equiv CH$ | 2 | m.p. 156–157° |
| 5-F | H | O | $-CH_2-CH_2-C\equiv CH$ | 2 | |
| 5-F | H | O | $-CH_2-C\equiv C-CH_3$ | 2 | |
| 5-CH(CH$_3$)$_2$ | H | O | $-CH_2-C\equiv CH$ | 2 | |
| 5-CH(CH$_3$)$_2$ | H | O | $-CH_2-CH_2-C\equiv CH$ | 2 | |
| 5-CH(CH$_3$)$_2$ | H | O | $-CH_2-C\equiv C-CH_3$ | 2 | |
| 5-CH$_3$ | H | O | $-CH_2-C\equiv CH$ | 2 | m.p. 169–171° |
| 5-CH$_3$ | H | O | $-CH_2-C\equiv C-CH_3$ | 2 | |
| 5-CH$_3$ | H | O | $-CH_2-CH_2-C\equiv CH$ | 2 | |
| 5-NO$_2$ | H | O | $-CH_2-C\equiv CH$ | 2 | |
| 5-NO$_2$ | H | O | $-CH_2-CH_2-C\equiv CH$ | 2 | |
| 5-NO$_2$ | H | O | $-CH_2-C\equiv C-CH_3$ | 2 | |
| 5-OCH$_3$ | H | O | $-CH_2-C\equiv C-CH_3$ | 2 | |
| 5-OCH$_3$ | H | O | $-CH_2-C\equiv CH$ | 2 | |
| 5-OCH$_3$ | H | O | $-CH_2-CH_2-C\equiv CH$ | 2 | |
| 5-CON(CH$_3$)$_2$ | H | O | $-CH_2-C\equiv CH$ | 2 | |
| 5-CON(CH$_3$)$_2$ | H | O | $-CH_2-C\equiv C-CH_3$ | 2 | |
| 5-COOCH$_3$ | H | O | $-CH_2-C\equiv CH$ | 2 | |
| 5-COOCH$_3$ | H | O | $-CH_2-C\equiv C-CH_3$ | 2 | |
| 5-COOCH$_3$ | H | O | $-CH_2-CH_2-C\equiv CH$ | 2 | |
| 5-NO$_2$ | 3-CF$_3$ | O | $-CH_2-C\equiv CH$ | 2 | |
| 5-NO$_2$ | 3-Cl | O | $-CH_2-C\equiv CH$ | 2 | |
| 5-NO$_2$ | 3-Cl | O | $-CH_2-C\equiv C-CH_3$ | 2 | |
| 5-CF$_3$ | 3-NO$_2$ | O | $-CH_2-C\equiv CH$ | 2 | |
| 5-CH$_3$ | 3-CH$_3$ | O | $-CH_2-C\equiv CH$ | 2 | |
| 5-CH$_3$ | 3-CH$_3$ | O | $-CH_2-CH_2-C\equiv CH$ | 2 | |
| 5-Cl | 3-NO$_2$ | O | $-CH_2-C\equiv CH$ | 2 | |
| 5-Cl | 3-Cl | O | $-CH_2-C\equiv CH$ | 2 | |
| 5-Cl | 3-Cl | O | $-CH_2-C\equiv C-CH_3$ | 2 | |
| 5-Cl | 3-Cl | O | $-CH_2-CH_2-C\equiv CH$ | 2 | |
| 5-Br | 3-OCH$_3$ | O | $-CH_2-C\equiv CH$ | 2 | |
| 5-Br | 2-OCH$_3$ | O | $-CH_2-C\equiv CH$ | 3 | |
| 3-OCH$_3$ | 5-COOCH$_3$ | O | $-CH_2-C\equiv CH$ | 2 | |
| 2-OCH$_3$ | 5-COOCH$_3$ | O | $-CH_2-C\equiv CH$ | 3 | |
| 5-CH$_3$ | 3-Br | O | $-CH_2-C\equiv CH$ | 2 | |
| 5-Br | 3-NO$_2$ | O | $-CH_2-C\equiv CH$ | 2 | |
| 5-Cl | 3-Br | O | $-CH_2-C\equiv CH$ | 2 | |
| 5-Cl | 3-Br | O | $-CH_2-C\equiv C-CH_3$ | 2 | |
| 5-Cl | 3-Br | O | $-CH_2-CH_2-C\equiv CH$ | 2 | |
| 5-CH(CH$_3$)$_2$ | 3-CH$_3$ | O | $-CH_2-CH_2-C\equiv CH$ | 2 | |
| 5-CH(CH$_3$)$_2$ | 3-CH$_3$ | O | $-CH_2-C\equiv C-CH_3$ | 2 | |
| 5-CH(CH$_3$)$_2$ | 3-CH$_3$ | O | $-CH_2-C\equiv CH$ | 2 | |
| 3-NO$_2$ | H | O | $-CH_2-C\equiv CH$ | 2 | |

TABLE 1-continued

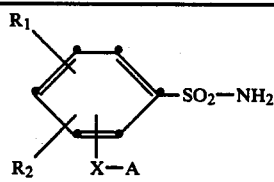

| R₁ | R₂ | X | A | Position of X-A | Physical data |
|---|---|---|---|---|---|
| 3-CH₃ | H | O | —CH₂—C≡CH | 2 | |
| 3-NO₂ | H | O | —CH₂—C≡CH | 2 | |
| 3-Cl | H | O | —CH₂—C≡CH | 2 | |
| 3-Cl | H | O | —CH₂—C≡C—CH₃ | 2 | |
| 3-Cl | H | O | —CH₂—CH₂—C≡CH | 2 | |
| 3-OCH₃ | H | O | —CH₂—C≡CH | 2 | |
| 3-OCH₃ | H | O | —CH₂—C≡C—CH₃ | 2 | |
| 2-OCH₃ | H | O | —CH₂—C≡CH | 2 | |
| H | H | SO | —CH₂—C≡CH | 2 | |
| H | H | SO₂ | —CH₂—C≡CH | 2 | |
| H | H | SO | —CH₂—C≡C—CH₃ | 2 | |
| H | H | SO₂ | —CH₂—C≡C—CH₂ | 2 | |
| 2-Cl | H | O | —CH₂—C≡CH | 5 | m.p. 149° |
| 6-Cl | 4-Br | o | —CH₂—C≡CH | 3 | m.p. 174° |

TABLE 2

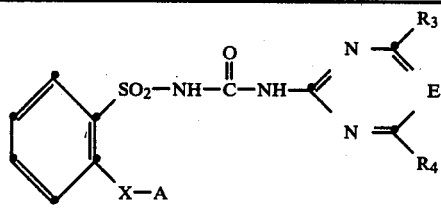

| No. | A | R₃ | R₄ | X | E | Physical Data |
|---|---|---|---|---|---|---|
| 1 | —CH₂—C≡CH | CH₃ | C₂H₅ | S | N | |
| 2 | —CH₂—C≡CH | OCH₃ | C₂H₅ | S | N | |
| 3 | —CH₂—C≡CH | CH₃ | OCH₃ | S | CH | |
| 4 | —CH₂—C≡CH | OCH₃ | OCH₃ | S | CH | |
| 5 | —CH₂—C≡CH | CH₃ | OCH₃ | SO | N | |
| 6 | —CH₂—C≡CH | OCH₃ | OCH₃ | SO | N | |
| 7 | —CH₂—C≡CH | CH₃ | C₂H₅ | SO | N | |
| 8 | —CH₂—C≡CH | —CH(CH₃)₂ | OCH₃ | O | CH | m.p. 129–130° |
| 9 | —CH₂—C≡CH | OCH₃ | SC₂H₅ | O | CH | |
| 10 | —CH₂—C≡CH | OCH₃ | SC₂H₅ | O | N | |
| 11 | —CH₂—C≡CH | OCH₃ | —SCH(CH₃)₂ | O | N | |
| 12 | —CH₂—C≡CH | CCl | CH₃ | O | N | m.p. 179–180° |
| 13 | —CH₂—C≡CH | CH₃ | Br | O | N | |
| 14 | —CH₂—C≡CH | CHF₂ | OCH₃ | O | N | m.p. 166–167° |
| 15 | —CH₂—C≡CH | CHF₂ | CH₃ | O | N | |
| 16 | —CH₂—C≡CH | —OCH₂CF₃ | Cl | O | N | |
| 17 | —CH₂—C≡CH | —OCH₂CF₃ | OCH₃ | O | N | m.p. 113–115° |
| 18 | —CH₂—C≡CH | —CH₂CF₃ | CH₃ | O | N | |
| 19 | —CH₂—C≡CH | OC₂H₅ | OC₂H₅ | O | N | m.p. 138–139° |
| 20 | —CH₂—C≡CH | OC₂H₅ | O | CH | | |
| 21 | —CH₂—C≡CH | C₂H₅ | OCH₃ | O | N | m.p. 134–135° |
| 22 | —CH₂—C≡CH | C₂H₅ | OC₂H₅ | O | N | |
| 23 | —CH₂—C≡CH | CH₃ | OC₂H₅ | O | N | m.p. 129–130° |
| 24 | —CH₂—C≡CH | CH₃ | CH₃ | O | CH | |
| 25 | —CH₂—C≡CH | CH₃ | OCH₃ | O | CH | m.p. 156–159° |
| 26 | —CH₂—C≡CH | CH₃ | —OCH₂—CF₃ | O | N | |
| 27 | —CH₂—C≡CH | CH₃ | H | O | N | m.p. 186–187° |
| 28 | —CH₂—C≡CH | C₂H₅ | Cl | O | CH | |
| 29 | —CH₂—C≡CH | CH₃ | Cl | O | CH | m.p. 225–227° |
| 30 | —CH₂—C≡CH | CH₃ | SCH₃ | O | CH | |
| 31 | —CH₂—C≡CH | CH₃ | F | O | CH | |
| 32 | —CH₂—C≡CH | CH₃ | Br | O | CH | |
| 33 | —CH₂—C≡CH | C₂H₅ | OC₂H₅ | O | CH | |
| 34 | —CH₂—C≡CH | C₂H₅ | SCH₃ | O | CH | |
| 35 | —CH₂—C≡CH | CF₃ | CH₃ | O | CH | |
| 36 | —CH₂—C≡CH | CH₂Cl | CH₃ | O | CH | |
| 37 | —CH₂—C≡CH | CH₂Cl | OCH₃ | O | CH | |
| 38 | —CH₂—C≡CH | OCH₃ | Cl | O | CH | m.p. 209–210° |
| 39 | —CH₂—C≡CH | Cl | Cl | O | CH | |
| 40 | —CH₂—C≡CH | OCH₃ | SCH₃ | O | CH | |

TABLE 2-continued

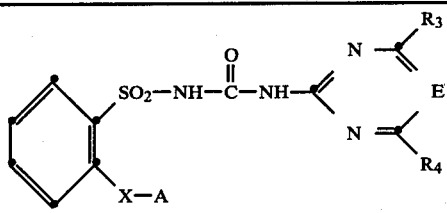

| No. | A | R3 | R4 | X | E | Physical Data |
|---|---|---|---|---|---|---|
| 41 | —CH2—C≡CH | OCH3 | —OCH(CH3)2 | O | CH | |
| 42 | —CH2—C≡CH | CH2F | OCH3 | O | CH | |
| 43 | —CH2—C≡CH | CHF2 | CH3 | O | CH | m.p. 189–192° |
| 44 | —CH2—C≡CH | CF3 | OCH3 | O | CH | |
| 45 | —CH2—C≡CH | C2H5 | —OCH(CH3)2 | O | N | |
| 46 | —CH2—C≡CH | C2H5 | Cl | O | N | |
| 47 | —CH2—C≡CH | C2H5 | SCH3 | O | N | |
| 48 | —CH2—C≡CH | C2H5 | CH3 | O | N | m.p. 132–134° |
| 49 | —CH2—C≡CH | C2H5 | C2H5 | O | N | |
| 50 | —CH2—C≡CH | OCH3 | —OCH(CH3)2 | O | N | m.p. 93–95° |
| 51 | —CH2—C≡CH | OCH3 | —OCH(CH3)—CH2—CH3 | O | N | |
| 52 | —CH2—C≡CH | CH3 | —CH(CH3)2 | O | N | |
| 53 | —CH2—C≡CH | —CH(CH3)2 | Cl | O | N | m.p. 120–121° |
| 54 | —CH2—C≡CH | —CH(CH3)2 | OCH3 | O | N | |
| 55 | —CH2—C≡CH | —CH(CH3)2 | OC2H5 | O | N | |
| 56 | —CH2—C≡CH | —CH(CH3)2 | SCH3 | O | N | |
| 57 | —CH2—C≡CH | CH2Cl | CH3 | O | N | |
| 58 | —CH2—C≡CH | CH2Cl | OCH3 | O | N | |
| 59 | —CH2—C≡CH | CH3F | CH3 | O | N | |
| 60 | —CH2—C≡CH | CH2F | OCH3 | O | N | |
| 61 | —CH2—C≡CH | CH2F | OC2H5 | O | N | |
| 62 | —CH2—C≡CH | —CH2—OCH3 | C2H5 | O | N | |
| 63 | —CH2—C≡CH | —CH2—SCH3 | OCH3 | O | N | |
| 64 | —CH2—C≡CH | —CH2—SCH3 | CH3 | O | N | |
| 65 | —CH2—C≡CH | —CH2—SCH3 | SCH3 | O | N | |
| 66 | —CH2—C≡CH | —CH2—SCH3 | Cl | O | N | |
| 67 | —CH2—C≡CH | —CH2—SCH3 | OC2H5 | O | N | |
| 68 | —CH2—C≡CH | SCH3 | Cl | O | N | m.p. 139–140° |
| 69 | —CH2—C≡CH | SCH3 | OCH3 | O | N | |
| 70 | —CH2—C≡CH | SCH3 | C2H5 | O | N | |
| 71 | —CH2—C≡CH | SCH3 | —OCH(CH3)2 | O | N | |
| 72 | —CH2—C≡CH | —OCH(CH3)2 | Cl | O | N | |
| 73 | —CH2—C≡CH | CF3 | OCH3 | O | N | |
| 74 | —CH2—C≡CH | Cf3 | CH3 | O | N | |
| 75 | —CH2—C≡CH | CF3 | OC2H5 | O | N | |
| 76 | —CH2—C≡CH | CCl | OCH3 | O | N | |
| 77 | —CH2—C≡CH | CCl3 | SCH3 | O | N | |
| 78 | —CH2—C≡CH | CH3 | Cl | O | N | |
| 79 | —CH2—C≡CH | OCH3 | Cl | O | N | m.p. 148–154° |
| 80 | —CH2—C≡CH | OCH3 | F | O | N | |
| 81 | —CH2—C≡CH | OCH3 | Br | O | N | |
| 82 | —CH2—C≡CH | CH3 | F | O | N | |
| 83 | —CH2—C≡CH | OCH3 | OCH3 | O | CH | |
| 84 | —CH2—C≡CH | CH3 | CH3 | O | N | m.p. 175–177° |
| 85 | —CH2—C≡CH | OCH3 | OC2H5 | O | N | |
| 86 | —CH2—C≡CH | OCH3 | OC2H5 | O | CH | |
| 87 | —CH2—C≡CH | —CH2—OCH3 | OCH3 | O | CH | m.p. 162–163° |
| 88 | —CH2—C≡CH | —CH2—OCH3 | OCH3 | O | N | |
| 89 | —CH2—C≡CH | C2H5 | OCH3 | O | CH | |
| 90 | —CH2—C≡CH | —CH2—OCH3 | CH3 | O | N | |
| 91 | —CH2—C≡CH | CH3 | OCH3 | S | N | |
| 92 | —CH2—C≡CH | OCH3 | OCH3 | S | N | |
| 93 | —CH2—C≡CH | CH3 | OCH3 | O | N | m.p. 157–158° |
| 94 | —CH2—C≡CH | OCH3 | OCH3 | O | N | m.p. 130–132° |
| 95 | —CH2—C≡C—CH3 | CH2Cl | OCH3 | O | N | |
| 96 | —CH2—C≡C—CH3 | CH2F | OCH3 | O | N | |
| 97 | —CH2—C≡C—CH3 | CH3 | OCH3 | O | CH | |
| 98 | —CH2—C≡C—CH3 | OCH3 | OCH3 | O | CH | |
| 99 | —CH2—C≡C—CH3 | CH3 | CH3 | O | CH | |
| 100 | —CH2—C≡C—CH3 | C2H5 | OCH3 | O | CH | |
| 101 | —CH2—C≡C—CH3 | OCH3 | Cl | O | CH | |
| 102 | —CH2—C≡C—CH3 | CH3 | Cl | O | CH | |
| 103 | —CH2—C≡C—CH3 | CF3 | OCH3 | O | CH | |
| 104 | —CH2—C≡C—CH3 | —CH2—OCH3 | OCH3 | O | CH | |
| 105 | —CH2—C≡C—CH3 | Br | OCH3 | O | CH | |
| 106 | —CH2—C≡C—CH3 | Br | CH3 | O | CH | |
| 107 | —CH2—C≡C—CH3 | OCH3 | SCH3 | O | CH | |
| 108 | —CH2—C≡C—CH3 | CH3 | SCH3 | O | CH | |
| 109 | —CH2—C≡C—CH3 | OCH3 | OC2H5 | O | CH | |
| 110 | —CH2—C≡C—CH3 | CH3 | CH3 | O | N | |

TABLE 2-continued

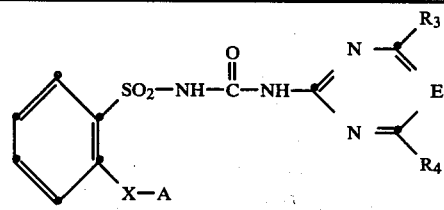

| No. | A | R3 | R4 | X | E | Physical Data |
|---|---|---|---|---|---|---|
| 111 | —CH$_2$—C≡C—CH$_3$ | CH$_3$ | OCH$_3$ | O | N | |
| 112 | —CH$_2$—C≡C—CH$_3$ | OCH$_3$ | OCH$_3$ | O | N | |
| 113 | —CH$_2$—C≡C—CH$_3$ | OCH$_3$ | OC$_2$H$_5$ | O | N | |
| 114 | —CH$_2$—C≡C—CH$_3$ | C$_2$H$_5$ | OCH$_3$ | O | N | |
| 115 | —CH$_2$—C≡C—CH$_3$ | C$_2$H$_5$ | CH$_3$ | O | N | |
| 116 | —CH$_2$—C≡C—CH$_3$ | Cl | OCH$_3$ | O | N | |
| 117 | —CH$_2$—C≡C—CH$_3$ | —OCH(CH$_3$)$_2$ | OCH$_3$ | O | N | |
| 118 | —CH$_2$—C≡C—CH$_3$ | —OCH(CH$_3$)$_2$ | OCH$_3$ | O | N | |
| 119 | —CH$_2$—C≡C—CH$_3$ | —OCH(CH$_3$)$_2$ | CH$_3$ | O | N | |
| 120 | —CH$_2$—C≡C—CH$_3$ | OCH$_3$ | SCH$_3$ | O | N | |
| 121 | —CH$_2$—C≡C—CH$_3$ | OC$_2$H$_5$ | OC$_2$H$_5$ | O | N | |
| 122 | —CH$_2$—C≡C—CH$_3$ | OCH$_3$ | —CH$_2$—OCH$_3$ | O | N | |
| 123 | —CH$_2$—CH$_2$—C≡CH | CH$_3$ | OCH$_3$ | O | N | |
| 124 | —CH$_2$—CH$_2$—C≡CH | CH$_3$ | CH$_3$ | O | N | |
| 125 | —CH$_2$—CH$_2$—C≡CH | C$_2$H$_5$ | OCH$_3$ | O | N | |
| 126 | —CH$_2$—CH$_2$—C≡CH | C$_2$H$_5$ | CH$_3$ | O | N | |
| 127 | —CH$_2$—CH$_2$—C≡CH | OCH$_3$ | OCH$_3$ | O | N | |
| 128 | —CH$_2$—CH$_2$—C≡CH | OCH$_3$ | OC$_2$H$_5$ | O | N | |
| 129 | —CH$_2$—CH$_2$—C≡CH | OC$_2$H$_5$ | OC$_2$H$_5$ | O | N | |
| 130 | —CH$_2$—CH$_2$—C≡CH | —CH$_2$—OCH$_3$ | OCH$_3$ | O | N | |
| 131 | —CH$_2$—CH$_2$—C≡CH | CH$_3$ | OCH$_3$ | O | CH | |
| 132 | —CH$_2$—CH$_2$—C≡CH | OCH$_3$ | OCH$_3$ | O | CH | |
| 133 | —CH$_2$—CH$_2$—C≡CH | CH$_3$ | CH$_3$ | O | CH | |
| 134 | —CH$_2$—CH$_2$—C≡CH | —CH$_2$—OCH$_3$ | OCH$_3$ | O | CH | |
| 135 | —CH$_2$—CH$_2$—C≡CH | CH$_3$ | Cl | O | CH | |
| 136 | —CH$_2$—CH$_2$—C≡CH | OCH$_3$ | Cl | O | CH | |
| 137 | —CH$_2$—CH$_2$—C≡CH | OCH$_3$ | OC$_2$H$_5$ | O | CH | |
| 138 | —CH$_2$C≡CH | CH$_3$ | —OCF$_2$—CHFCl | O | CH | m.p. 153–155° |
| 139 | —CH$_2$—C≡CH | CH$_3$ | —OCF$_2$—CHF$_2$ | O | CH | m.p. 171–173° |

TABLE 3

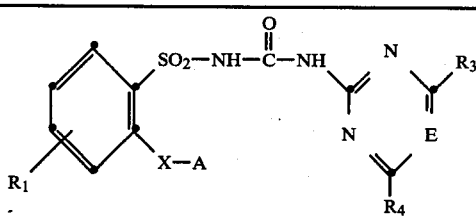

| No. | A | R$_1$ | R$_3$ | R$_4$ | X | E | Physical data |
|---|---|---|---|---|---|---|---|
| 201 | —CH$_2$—C≡CH | 6-Cl | CH$_3$ | OCH$_3$ | O | N | |
| 202 | —CH$_2$—C≡CH | 6-Cl | CH$_3$ | OCH$_3$ | O | CH | |
| 203 | —CH$_2$—C≡CH | 6-Cl | C$_2$H$_5$ | OCH$_3$ | O | N | |
| 204 | —CH$_2$—C≡CH | 6-Cl | OCH$_3$ | OCH$_3$ | O | CH | |
| 205 | —CH$_2$—C≡CH | 6-Cl | OCH$_3$ | OCH$_3$ | O | N | |
| 206 | —CH$_2$—C≡C—CH$_3$ | 6-Cl | OCH$_3$ | CH$_3$ | O | N | |
| 207 | —CH$_2$—C≡C—CH$_3$ | 6-Cl | OCH$_3$ | CH$_3$ | O | CN | |
| 208 | —CH$_2$—CH$_2$—C≡CH | 6-Cl | OCH$_3$ | CH$_3$ | O | N | |
| 209 | —CH$_2$—C≡CH | 6-OCH$_3$ | CH$_3$ | OCH$_3$ | O | CH | |
| 210 | —CH$_2$—C≡CH | 6-OCH$_3$ | CH$_3$ | OCH$_3$ | O | N | |
| 211 | —CH$_2$—C≡CH | 6-OCH$_3$ | C$_2$H$_5$ | OCH$_3$ | O | N | |
| 212 | —CH$_2$—C≡CH | 6-OCH$_3$ | OCH$_3$ | OCH$_3$ | O | N | |
| 213 | —CH$_2$—C≡CH | 6-OCH$_3$ | OCH$_3$ | OCH$_3$ | O | CH | |
| 214 | —CH$_2$—C≡CH | 6-CH$_3$ | CH$_3$ | OCH$_3$ | O | N | |
| 215 | —CH$_2$—C≡CH | 6-CH$_3$ | CH$_3$ | CH$_3$ | O | CH | |
| 216 | —CH$_2$—C≡CH | 6-CH$_3$ | OCH$_3$ | OCH$_3$ | O | CH | |
| 217 | —CH$_2$—C≡CH | 6-CH$_3$ | OCH$_3$ | OCH$_3$ | O | N | |
| 218 | —CH$_2$—C≡CH | 6-NO$_2$ | CH$_3$ | OCH$_3$ | O | N | |
| 219 | —CH$_2$—C≡CH | 6-NO$_2$ | CH$_3$ | OCH$_3$ | O | CH | |
| 220 | —CH$_2$—C≡CH | 6-NO$_2$ | OCH$_3$ | OCH$_3$ | O | CH | |
| 221 | —CH$_2$—C≡CH | 6-NO$_2$ | OCH$_3$ | OCH$_3$ | O | N | |
| 222 | —CH$_2$—C≡CH | 6-COOCH$_3$ | OCH$_3$ | OCH$_3$ | O | CH | |
| 223 | —CH$_2$—C≡CH | 6-COOCH$_3$ | CH$_3$ | CH$_3$ | O | N | |
| 224 | —CH$_2$—C≡CH | 6-COOCH$_3$ | OCH$_3$ | OCH$_3$ | O | N | |

TABLE 3-continued

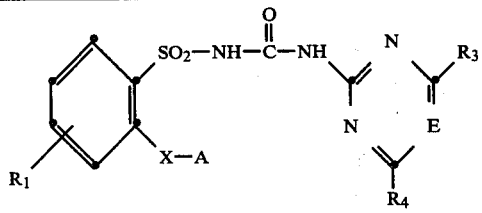

| No. | A | R₁ | R₃ | R₄ | X | E | Physical data |
|---|---|---|---|---|---|---|---|
| 292 | —CH₂—C≡CH | H | OCHF₂ | OCH₃ | O | CH | |
| 293 | —CH₂—C≡CH | H | OCHF₂ | Cl | O | CH | |
| 294 | —CH₂—C≡CH | H | CH₃ | —OCF₂—CHF₂ | O | CH | |
| 295 | —CH₂—C≡CH | H | OCH₃ | —OCF₂—CHF₂ | O | CH | |
| 296 | —CH₂—C≡CH | H | Cl | —OCF₂—CHF₂ | O | CH | |
| 297 | —CH₂—C≡CH | H | CH₃ | —OCF₂—CHFCl | O | CH | |
| 298 | —CH₂—C≡CH | H | OCH₃ | —OCF₂—CHFCl | O | CH | |
| 299 | —CH₂—C≡CH | H | Cl | —OCF₂—CHFCl | O | CH | |
| 300 | —CH₂—C≡CH | 5-Cl | CH₃ | CH₃ | O | CH | m.p. 206–208° (decomp.) |
| 301 | —CH₂—C≡CH | 5-F | CH₃ | CH₃ | O | CH | m.p. 219–220° (decomp.) |

TABLE 4

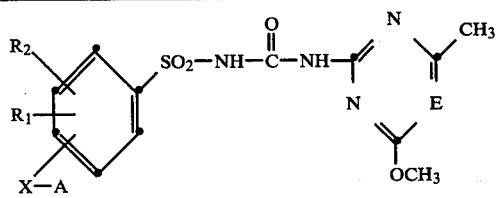

| No. | A | Position of X-A | R₁ | R₂ | X | E | Physical data |
|---|---|---|---|---|---|---|---|
| 401 | —CH₂—C≡CH | 5 | 2-CH₃ | H | O | N | |
| 402 | —CH₂—C≡C—CH₃ | 5 | 2-CH₃ | H | O | CH | |
| 403 | —CH₂—CH₂—C≡CH | 5 | 2-CH₃ | H | O | CH | |
| 404 | —CH₂—CH₂—C≡CH | 5 | 2-CH₃ | H | O | N | |
| 405 | —CH₂—C≡C—CH₃ | 5 | 2-CH₃ | H | O | N | |
| 406 | —CH₂—C≡CH | 5 | 2-CH₃ | H | O | CH | |
| 407 | —CH₂—C≡CH | 5 | 2-Cl | H | O | N | m.p. 175–176° |
| 408 | —CH₂—C≡CH | 5 | 2-Cl | H | O | CH | |
| 409 | —CH₂—C≡C—CH₃ | 5 | 2-Cl | H | O | CH | |
| 410 | —CH₂—C≡C—CH₃ | 5 | 2-Cl | H | O | N | |
| 411 | —CH₂—CH₂—C≡CH | 5 | 2-Cl | H | O | N | |
| 412 | —CH₂—CH₂—C≡CH | 5 | 2-Cl | H | O | CH | |
| 413 | —CH₂—CH₂—C≡CH | 5 | 2-CH₃ | H | O | N | |
| 414 | —CH₂—C≡CH | 3 | 2-CH₃ | H | O | CH | |
| 415 | —CH₂—C≡C—CH₃ | 3 | 2-CH₃ | H | O | CH | |
| 416 | —CH₂—C≡CH | 3 | 2-CH₃ | H | O | N | |
| 417 | —CH₂—C≡CH | 3 | 2-OCH₃ | H | O | CH | |
| 418 | —CH₂—C≡CH | 3 | 2-OCH₃ | H | O | N | |
| 419 | —CH₂—C≡C—CH₃ | 3 | 2-OCH₃ | H | O | N | |
| 420 | —CH₂—C≡C—CH₃ | 3 | 2-OCH₃ | H | O | CH | |
| 421 | —CH₂—CH₂—C≡CH | 3 | 2-OCH₃ | H | O | CH | |
| 422 | —CH₂—CH₂—C≡CH | 3 | 2-OCH₃ | H | O | N | |
| 423 | —CH₂—C≡CH | 5 | 2-OCH₃ | H | O | N | |
| 424 | —CH₂—C≡CH | 5 | 2-OCH₃ | H | O | CH | |
| 425 | —CH₂—C≡C—CH₃ | 5 | 2-OCH₃ | H | O | CH | |
| 426 | —CH₂—C≡C—CH₃ | 5 | 2-OCH₃ | H | O | N | |
| 427 | —CH₂—CH₂—C≡CH | 5 | 2-OCH₃ | H | O | N | |
| 428 | —CH₂—CH₂—C≡CH | 5 | 2-OCH₃ | H | O | CH | |
| 429 | —CH₂—C≡CH | 3 | 5-Br | 2-OCH₃ | O | N | |
| 430 | —CH₂—C≡CH | 3 | 5-Br | 2-OCH₃ | O | CH | |
| 431 | —CH₂—C≡C—CH₃ | 3 | 5-Br | 2-OCH₃ | O | CH | |
| 432 | —CH₂—C≡C—CH₃ | 3 | 5-Br | 2-OCH₃ | O | N | |
| 433 | —CH₂—C≡CH | 3 | 5-COOCH₃ | 2-OCH₃ | O | N | |
| 434 | —CH₂—C≡CH | 3 | 5-COOCH₃ | 2-OCH₃ | O | CH | |
| 435 | —CH₂—CH₂—C≡CH | 3 | 5-COOCH₃ | 2-OCH₃ | O | CH | |
| 436 | —CH₂—CH₂—C≡CH | 3 | 5-COOCH₃ | 2-OCH₃ | O | N | |
| 437 | —CH₂—C≡CH | 3 | 5-COOCH₃ | 2-OCH₃ | O | N | |
| 438 | —CH₂—C≡CH | 3 | 5-COOCH₃ | 2-OCH₃ | O | CH | |
| 439 | —CH₂—C≡CH | 2 | 5-NO₂ | 3-CF₃ | O | N | |
| 440 | —CH₂—C≡CH | 2 | 5-NO₂ | 3-CF₃ | O | CH | |
| 441 | —CH₂—C≡CH | 2 | 5-NO₂ | 3-Cl | O | CH | |

TABLE 3-continued

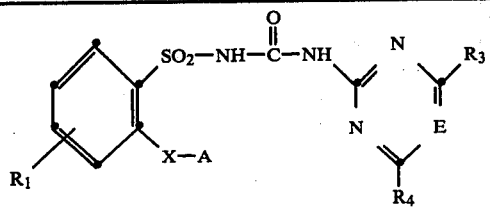

| No. | A | R₁ | R₃ | R₄ | X | E | Physical data |
|---|---|---|---|---|---|---|---|
| 225 | —CH₂—C≡CH | 6-COOCH₃ | OCH₃ | OCH₃ | O | CH | |
| 226 | —CH₂—C≡CH | 5-Cl | CH₃ | OCH₃ | O | N | m.p. 177° |
| 227 | —CH₂—C≡CH | 5-Cl | CH₃ | OCH₃ | O | CH | m.p. 208° |
| 228 | —CH₂—C≡CH | 5-Cl | OCH₃ | OCH₃ | O | N | |
| 229 | —CH₂—C≡CH | 5-Cl | OCH₃ | OCH₃ | O | N | |
| 230 | —CH₂—C≡CH | 5-Cl | C₂H₅ | CH₃ | O | N | |
| 231 | —CH₂—CH₂—C≡CH | 5-Cl | CH₃ | OCH₃ | O | N | |
| 232 | —CH₂—CH₂—C≡CH | 5-Cl | CH₃ | OCH₃ | O | CH | |
| 233 | —CH₂—C≡C—CH₃ | 5-Cl | CH₃ | OCH₃ | O | CH | |
| 234 | —CH₂—C≡C—CH₃ | 5-Cl | CH₃ | OCH₃ | O | N | |
| 235 | —CH₂—C≡C—CH₃ | 5-Cl | C₂H₅ | OCH₃ | O | N | |
| 236 | —CH₂—C≡C—CH₃ | 5-Cl | OCH₃ | OCH₃ | O | N | |
| 237 | —CH₂—C≡C—CH₃ | 5-Cl | OCH₃ | OCH₃ | O | CH | |
| 238 | —CH₂—C≡CH | 5-F | CH₃ | OCH₃ | O | N | m.p. 158° |
| 239 | —CH₂—C≡CH | 5-F | CH₃ | OCH₃ | O | CH | m.p. 211° (decomp.) |
| 240 | —CH₂—C≡CH | 5-F | OCH₃ | C₂H₅ | O | N | |
| 241 | —CH₂—C≡CH | 5-F | OCH₃ | OCH₃ | O | CH | |
| 242 | —CH₂—C≡CH | 5-NO₂ | OCH₃ | OCH₃ | O | N | |
| 243 | —CH₂—C≡CH | 5-NO₂ | CH₃ | CH₃ | O | N | |
| 244 | —CH₂—C≡CH | 5-NO₂ | CH₃ | OCH₃ | O | CH | |
| 245 | —CH₂—C≡CH | 5-CH(CH₃)₂ | CH₃ | OCH₃ | O | N | |
| 246 | —CH₂—C≡CH | 5-CH(CH₃)₂ | CH₃ | OCH₃ | O | CH | |
| 247 | —CH₂—C≡CH | 5-CH(CH₃)₂ | C₂H₅ | OCH₃ | O | N | |
| 248 | —CH₂—C≡CH | 5-CH(CH₃)₂ | OCH₃ | OCH₃ | O | N | |
| 249 | —CH₂—CH₂—C≡CH | 5-CH(CH₃)₂ | OCH₃ | OCH₃ | O | N | |
| 250 | —CH₂—CH₂—C≡CH | 5-CH(CH₃)₂ | OCH₃ | CH₃ | O | N | |
| 251 | —CH₂—CH₂—C≡CH | 5-CH(CH₃)₂ | OCH₃ | OCH₃ | O | CH | |
| 252 | —CH₂—C≡C—CH₃ | 5-CH(CH₃)₂ | OCH₃ | OCH₃ | O | N | |
| 253 | —CH₂—C≡C—CH₃ | 5-CH(CH₃)₂ | OCH₃ | OCH₃ | O | CH | |
| 254 | —CH₂—C≡C—CH₃ | 5-CH(CH₃)₂ | OCH₃ | CH₃ | O | N | |
| 255 | —CH₂—C≡C—CH₃ | 5-CH(CH₃)₂ | OCH₃ | CH₃ | O | CH | |
| 256 | —CH₂—C≡CH | 5-CH₃ | CH₃ | OCH₃ | O | N | |
| 257 | —CH₂—C≡CH | 5-CH₃ | CH₃ | OCHF₂ | O | CH | m.p. 201-203° |
| 258 | —CH₂—C≡CH | 5-CH₃ | C₂H₅ | OCH₃ | O | N | |
| 259 | —CH₂—C≡CH | 5-CH₃ | OCH₃ | OCH₃ | O | N | |
| 260 | —CH₂—C≡CH | 5-CH₃ | OCH₃ | OCH₃ | O | CH | |
| 261 | —CH₂—C≡CH | 5-OCH₃ | CH₃ | OCH₃ | O | CH | |
| 262 | —CH₂—C≡CH | 5-OCH₃ | OCH₃ | OCH₃ | O | CH | |
| 263 | —CH₂—C≡CH | 5-OCH₃ | OCH₃ | OCH₃ | O | N | |
| 264 | —CH₂—C≡CH | 5-OCH₃ | OCH₃ | C₂H₅ | O | N | |
| 265 | —CH₂—C≡CH | 5-COOCH₃ | CH₃ | OCH₃ | O | N | |
| 266 | —CH₂—C≡CH | 5-COOCH₃ | CH₃ | OCH₃ | O | CH | |
| 267 | —CH₂—C≡CH | 5-COOCH₃ | OCH₃ | OCH₃ | O | N | |
| 268 | —CH₂—C≡CH | 5-COOCH₃ | OCH₃ | OCH₃ | O | CH | |
| 269 | —CH₂—C≡CH | 3-NO₂ | CH₃ | OCH₃ | O | CH | |
| 270 | —CH₂—C≡CH | 3-NO₂ | CH₃ | OCH₃ | O | N | |
| 271 | —CH₂—C≡CH | 3-NO₂ | C₂H₅ | OCH₃ | O | N | |
| 272 | —CH₂—C≡CH | 3-NO₂ | OCH₃ | OCH₃ | O | N | |
| 273 | —CH₂—C≡CH | 3-OCH₃ | CH₃ | OCH₃ | O | N | |
| 274 | —CH₂—C≡CH | 3-OCH₃ | CH₃ | OCH₃ | O | CH | |
| 275 | —CH₂—C≡CH | 3-OCH₃ | OCH₃ | OCH₃ | O | CH | |
| 276 | —CH₂—C≡CH | 3-OCH₃ | C₂H₅ | OCH₃ | O | N | |
| 277 | —CH₂—C≡CH | 3-OCH₃ | OCH₃ | OCH₃ | O | N | |
| 278 | —CH₂—C≡CH | 3-CH₃ | OCH₃ | CH₃ | O | CH | |
| 279 | —CH₂—C≡CH | 3-CH₃ | C₂H₅ | CH₃ | O | N | |
| 280 | —CH₂—C≡CH | 3-CH₃ | OCH₃ | CH₃ | O | N | |
| 281 | —CH₂—C≡CH | 3-CH₃ | OCH₃ | CH₃ | O | CH | |
| 282 | —CH₂—C≡CH | 3-Cl | OCH₃ | CH₃ | O | CH | |
| 283 | —CH₂—C≡CH | 3-Cl | OCH₃ | CH₃ | O | N | |
| 284 | —CH₂—C≡CH | 3-Cl | OCH₃ | OCH₃ | O | N | |
| 285 | —CH₂—C≡CH | 3-Cl | OCH₃ | OCH₃ | O | CH | |
| 286 | —CH₂—C≡CH | 5-Br | OCH₃ | CH₃ | O | N | m.p. 187-188° |
| 287 | —CH₂—C≡CH | 5-CH₃ | CH₃ | OCH₃ | O | N | |
| 288 | —CH₂—C≡CH | 5-CH₃ | OCH₃ | Cl | O | CH | m.p. 202-204° |
| 289 | —CH₂—C≡CH | 5-F | OCH₃ | OCH₃ | O | N | m.p. 182-183° |
| 290 | —CH₂—C≡CH | 5-Cl | OCHF₂ | CH₃ | O | CH | m.p. 175-176° (decomp.) |
| 291 | —CH₂—C≡CH | 5-F | OCHF₂ | CH₃ | O | CH | m.p. 175° (decomp.) |

TABLE 3-continued

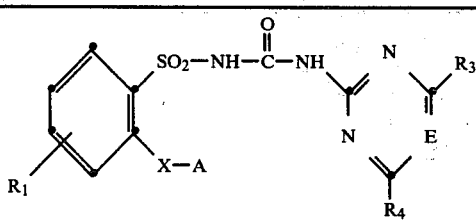

| No. | A | $R_1$ | $R_3$ | $R_4$ | X | E | Physical data |
|---|---|---|---|---|---|---|---|
| 292 | —$CH_2$—C≡CH | H | $OCHF_2$ | $OCH_3$ | O | CH | |
| 293 | —$CH_2$—C≡CH | H | $OCHF_2$ | Cl | O | CH | |
| 294 | —$CH_2$—C≡CH | H | $CH_3$ | —$OCF_2$—$CHF_2$ | O | CH | |
| 295 | —$CH_2$—C≡CH | H | $OCH_3$ | —$OCF_2$—$CHF_2$ | O | CH | |
| 296 | —$CH_2$—C≡CH | H | Cl | —$OCF_2$—$CHF_2$ | O | CH | |
| 297 | —$CH_2$—C≡CH | H | $CH_3$ | —$OCF_2$—CHFCl | O | CH | |
| 298 | —$CH_2$—C≡CH | H | $OCH_3$ | —$OCF_2$—CHFCl | O | CH | |
| 299 | —$CH_2$—C≡CH | H | Cl | —$OCF_2$—CHFCl | O | CH | |
| 300 | —$CH_2$—C≡CH | 5-Cl | $CH_3$ | $CH_3$ | O | CH | m.p. 206–208° (decomp.) |
| 301 | —$CH_2$—C≡CH | 5-F | $CH_3$ | $CH_3$ | O | CH | m.p. 219–220° (decomp.) |

TABLE 4

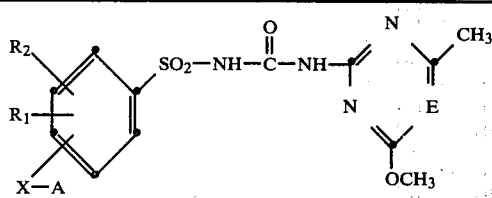

| No. | A | Position of X-A | $R_1$ | $R_2$ | X | E | Physical data |
|---|---|---|---|---|---|---|---|
| 401 | —$CH_2$—C≡CH | 5 | 2-$CH_3$ | H | O | N | |
| 402 | —$CH_2$—C≡C—$CH_3$ | 5 | 2-$CH_3$ | H | O | CH | |
| 403 | —$CH_2$—$CH_2$—C≡CH | 5 | 2-$CH_3$ | H | O | CH | |
| 404 | —$CH_2$—$CH_2$—C≡CH | 5 | 2-$CH_3$ | H | O | N | |
| 405 | —$CH_2$—C≡C—$CH_3$ | 5 | 2-$CH_3$ | H | O | N | |
| 406 | —$CH_2$—C≡CH | 5 | 2-$CH_3$ | H | O | CH | |
| 407 | —$CH_2$—C≡CH | 5 | 2-Cl | H | O | N | m.p. 175–176° |
| 408 | —$CH_2$—C≡CH | 5 | 2-Cl | H | O | CH | |
| 409 | —$CH_2$—C≡C—$CH_3$ | 5 | 2-Cl | H | O | CH | |
| 410 | —$CH_2$—C≡C—$CH_3$ | 5 | 2-Cl | H | O | N | |
| 411 | —$CH_2$—$CH_2$—C≡CH | 5 | 2-Cl | H | O | N | |
| 412 | —$CH_2$—$CH_2$—C≡CH | 5 | 2-Cl | H | O | CH | |
| 413 | —$CH_2$—$CH_2$—C≡CH | 5 | 2-$CH_3$ | H | O | N | |
| 414 | —$CH_2$—C≡CH | 3 | 2-$CH_3$ | H | O | CH | |
| 415 | —$CH_2$—C≡C—$CH_3$ | 3 | 2-$CH_3$ | H | O | CH | |
| 416 | —$CH_2$—C≡CH | 3 | 2-$CH_3$ | H | O | N | |
| 417 | —$CH_2$—C≡CH | 3 | 2-$OCH_3$ | H | O | CH | |
| 418 | —$CH_2$—C≡CH | 3 | 2-$OCH_3$ | H | O | N | |
| 419 | —$CH_2$—C≡C—$CH_3$ | 3 | 2-$OCH_3$ | H | O | N | |
| 420 | —$CH_2$—C≡C—$CH_3$ | 3 | 2-$OCH_3$ | H | O | CH | |
| 421 | —$CH_2$—$CH_2$—C≡CH | 3 | 2-$OCH_3$ | H | O | CH | |
| 422 | —$CH_2$—$CH_2$—C≡CH | 3 | 2-$OCH_3$ | H | O | N | |
| 423 | —$CH_2$—C≡CH | 5 | 2-$OCH_3$ | H | O | N | |
| 424 | —$CH_2$—C≡CH | 5 | 2-$OCH_3$ | H | O | CH | |
| 425 | —$CH_2$—C≡C—$CH_3$ | 5 | 2-$OCH_3$ | H | O | CH | |
| 426 | —$CH_2$—C≡C—$CH_3$ | 5 | 2-$OCH_3$ | H | O | N | |
| 427 | —$CH_2$—$CH_2$—C≡CH | 5 | 2-$OCH_3$ | H | O | N | |
| 428 | —$CH_2$—$CH_2$—C≡CH | 5 | 2-$OCH_3$ | H | O | CH | |
| 429 | —$CH_2$—C≡CH | 3 | 5-Br | 2-$OCH_3$ | O | N | |
| 430 | —$CH_2$—C≡CH | 3 | 5-Br | 2-$OCH_3$ | O | CH | |
| 431 | —$CH_2$—C≡C—$CH_3$ | 3 | 5-Br | 2-$OCH_3$ | O | CH | |
| 432 | —$CH_2$—C≡C—$CH_3$ | 3 | 5-Br | 2-$OCH_3$ | O | N | |
| 433 | —$CH_2$—C≡CH | 3 | 5-$COOCH_3$ | 2-$OCH_3$ | O | N | |
| 434 | —$CH_2$—C≡CH | 3 | 5-$COOCH_3$ | 2-$OCH_3$ | O | CH | |
| 435 | —$CH_2$—$CH_2$—C≡CH | 3 | 5-$COOCH_3$ | 2-$OCH_3$ | O | CH | |
| 436 | —$CH_2$—$CH_2$—C≡CH | 3 | 5-$COOCH_3$ | 2-$OCH_3$ | O | N | |
| 437 | —$CH_2$—C≡CH | 3 | 5-$COOCH_3$ | 2-$OCH_3$ | O | N | |
| 438 | —$CH_2$—C≡CH | 3 | 5-$COOCH_3$ | 2-$OCH_3$ | O | CH | |
| 439 | —$CH_2$—C≡CH | 2 | 5-$NO_2$ | 3-$CF_3$ | O | N | |
| 440 | —$CH_2$—C≡CH | 2 | 5-$NO_2$ | 3-$CF_3$ | O | CH | |
| 441 | —$CH_2$—C≡CH | 2 | 5-$NO_2$ | 3-Cl | O | CH | |

TABLE 4-continued

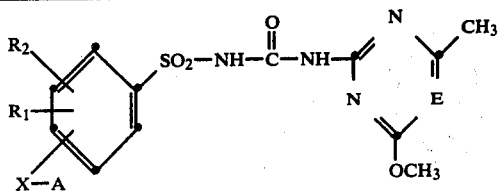

| No. | A | Position of X-A | R₁ | R₂ | X | E | Physical data |
|---|---|---|---|---|---|---|---|
| 442 | —CH₂—C≡CH | 2 | 5-NO₂ | 3-Cl | O | N | |
| 443 | —CH₂—C≡C—CH₃ | 2 | 5-NO₂ | 3-Cl | O | N | |
| 444 | —CH₂—C≡C—CH₃ | 2 | 5-NO₂ | 3-Cl | O | CH | |
| 445 | —CH₂—C≡CH | 2 | 5-CF₃ | 3-NO₂ | O | CH | |
| 446 | —CH₂—C≡CH | 2 | 5-CF₃ | 3-NO₂ | O | N | |
| 447 | —CH₂—C≡CH | 2 | 5-CH₃ | 3-CH₃ | O | N | |
| 448 | —CH₂—C≡CH | 2 | 5-CH₃ | 3-CH₃ | O | CH | |
| 449 | —CH₂—CH₂—C≡CH | 2 | 5-CH₃ | 3-CH₃ | O | CH | |
| 450 | —CH₂—CH₂—C≡CH | 2 | 5-CH₃ | | O | N | |
| 451 | —CH₂—C≡CH | 2 | 5-Cl | 3-NO₂ | O | N | |
| 452 | —CH₂—C≡CH | 2 | 5-Cl | 3-NO₂ | O | CH | |
| 453 | —CH₂—C≡C—CH₃ | 2 | 5-Cl | 3-NO₂ | O | CH | |
| 454 | —CH₂—C≡C—CH₃ | 2 | 5-Cl | 3-NO₂ | O | N | |
| 455 | —CH₂—C≡CH | 2 | 5-Cl | 3-Cl | O | N | |
| 456 | —CH₂—C≡CH | 2 | 5-Cl | 3-Cl | O | CH | |
| 457 | —CH₂—C≡C—CH₃ | 2 | 5-Cl | 3-Cl | O | CH | |
| 458 | —CH₂—C≡C—CH₃ | 2 | 5-Cl | 3-Cl | O | N | |
| 459 | —CH₂—CH₂—C≡CH | 2 | 5-Cl | 3-Cl | O | N | |
| 460 | —CH₂—CH₂—C≡CH | 2 | 5-Cl | 3-Cl | O | CH | |
| 461 | —CH₂—CH₂—C≡CH | 2 | 5-Br | 3-OCH₃ | O | N | |
| 462 | —CH₂—CH₂—C≡CH | 2 | 5-Br | 3-OCH₃ | O | CH | |
| 463 | —CH₂—C≡CH | 3 | 5-Br | 2-OCH₃ | O | CH | |
| 464 | —CH₂—C≡CH | 3 | 5-Br | 2-OCH₃ | O | N | |
| 465 | —CH₂—C≡CH | 2 | 5-COOCH₃ | 3-OCH₃ | O | N | |
| 466 | —CH₂—C≡CH | 2 | 5-COOCH₃ | 3-OCH₃ | O | CH | |
| 467 | —CH₂—C≡C—CH₃ | 3 | 5-COOCH₃ | 2-OCH₃ | O | CH | |
| 468 | —CH₂—C≡C—CH₃ | 3 | 5-COOCH₃ | 2-OCH₃ | O | N | |
| 469 | —CH₂—CH₂—C≡CH | 3 | 5-COOCH₃ | 2-OCH₃ | O | N | |
| 470 | —CH₂—CH₂—C≡CH | 3 | 5-COOCH₃ | 2-OCH₃ | O | CH | |
| 471 | —CH₃—CH₂—C≡CH | 3 | 5-CH₃ | 3-Br | O | CH | |
| 472 | —CH₂—CH₂—C≡CH | 2 | 5-CH₃ | 3-Br | O | N | |
| 473 | —CH₂—C≡CH | 2 | 5-CH₃ | 3-Br | O | N | |
| 474 | —CH₂—C≡CH | 2 | 5-CH₃ | 3-Br | O | CH | |
| 475 | —CH₂—C≡CH | 2 | 5-Br | 3-NO₂ | O | N | |
| 476 | —CH₂—C≡CH | 2 | 5-Br | 3-NO₂ | O | CH | |
| 477 | —CH₂—C≡CH | 2 | 5-Cl | 3-Br | O | N | |
| 478 | —CH₂—C≡C—CH₃ | 2 | 5-Cl | 3-Br | O | N | |
| 479 | —CH₂—C≡C—CH₃ | 2 | 5-Cl | 3-Br | O | CH | |
| 480 | —CH₂—C≡CH | 2 | 5-Cl | 3-Br | O | CH | |
| 481 | —CH₂—CH₂—C≡CH | 2 | 5-Cl | 3-Br | O | N | |
| 482 | —CH₂—C≡CH | 5 | 2-NO₂ | H | O | CH | |
| 483 | —CH₂—C≡CH | 5 | 2-NO₂ | H | O | N | |
| 484 | —CH₂—C≡CH | 5 | 2-Cl | H | O | N | |
| 485 | —CH₂—C≡CH | 5 | 2-Cl | H | O | CH | |
| 486 | —CH₂—C≡C—CH₃ | 5 | 2-Cl | H | O | CH | |
| 487 | —CH₂—C≡C—CH₃ | 5 | 2-Cl | H | O | N | |
| 488 | —CH₂—CH₂—C≡CH | 5 | 2-Cl | H | O | N | |
| 489 | —CH₂—CH₂—C≡CH | 5 | 2-Cl | H | O | CH | |

FORMULATION EXAMPLES

EXAMPLE 3

Formulation Examples for active ingredients of the formula I (%=percent by weight)

| (a) Wettable powder | (a) | (b) | (c) |
|---|---|---|---|
| active ingredient | 20% | 60% | 0.5% |
| sodium lignin sulfonate | 5% | 5% | 5% |
| sodium lauryl sulfate | 3% | — | — |
| sodium diisobutylnaphthalene sulfonate | — | 6% | 6% |
| octylphenolpolyethylene glycol ether (7–8 mols of ethylene oxide) | — | 2% | 2% |
| highly dispersed silicic acid | 5% | 27% | 27% |
| kaolin | 67% | — | — |
| sodium chloride | — | — | 59.5% |

The active ingredient is well mixed with the additives and ground in a suitable mill. There are obtained wettable powders which can be diluted with water to give suspensions of the concentration desired.

| (b) Emulsion concentrate | (a) | (b) |
|---|---|---|
| active ingredient | 10% | 1% |
| octylphenolpolyethylene glycol ether (4–5 mols of ethylene oxide) | 3% | 3% |
| calcium dodecyl benzene sulfonate | 3% | 3% |
| castor oil polyglycol ether | 4% | 4% |

-continued

| (b) Emulsion concentrate | (a) | (b) |
|---|---|---|
| (36 mols of ethylene oxide) cyclohexanone | 30% | 10% |
| xylene mixture | 50% | 79% |

Emulsions of the concentration desired can be obtained from this concentrate by dilution with water.

| (c) Dust | (a) | (b) |
|---|---|---|
| active ingredient | 0.1% | 1% |
| talcum | 99.9% | — |
| kaolin | — | 99% |

Dusts ready for use are obtained by mixing the active-ingredient with the carriers, and grinding the mixture in a suitable mill.

| (d) Extruder granulate | (a) | (b) |
|---|---|---|
| active ingredient | 10% | 1% |
| sodium lignin sulfonate | 2% | 2% |
| carboxymethylcellulose | 1% | 1% |
| kaolin | 87% | 96% |

The active ingredient is mixed with the additives, and the mixture is then ground and moistened with water. It is extruded and subsequently dried in a stream of air.

| (e) Coated granulate | |
|---|---|
| active ingredient | 3% |
| polyethylene glycol (MG 200) | 3% |
| kaolin | 94% |

The finely ground active ingredient is uniformuly applied, in a mixer, to the kaolin moistened with polyethylene glycol. Non-dusty coated granulates are obtained in this manner.

| (f) Suspension concentrate | (a) | (b) |
|---|---|---|
| active ingredient | 40% | 5% |
| ethylene glycol | 10% | 10% |
| nonylphenolpolyethylene glycol ether (15 mols of ethylene oxide) | 6% | 1% |
| sodium lignin sulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the additives. There is thus obtained a suspension concentrate from which can be produced, by dilution with water, suspensions of the concentration desired.

| (g) Salt solution | |
|---|---|
| active ingredient | 5% |
| isopropylamine | 1% |
| octylphenolpolyethylene glycol ether (78 mols of ethylene oxide) | 3% |
| water | 91%. |

BIOLOGICAL EXAMPLES

EXAMPLE 4

Verification of the herbicidal activity before emergence of the plants

Plant seeds are sown in flower pots (12–15 cm diameter) in a greenhouse. The surface of the soil is treated immediately afterwards with an aqueous dispersion or solution of the active ingredients, the concentration used being 4 kg of active ingredient per hectare. The pots are then kept in the greenhouse at a temperature of 22°–25° C. with 50–70% relative humidity. The test results are evaluated after 3 weeks, and the action on the test plants is assessed according to the following scale of ratings:

| | |
|---|---|
| 1 | plants have not emerged or are totally destroyed |
| 2–3 | very strong action |
| 4–6 | medium action |
| 7–8 | weak action |
| 9 | no action (as untreated control plants). |

Pre-emergence action
Applied amount: 4 kg of active ingredient/hectare

| Comp. No. | Avena | Setaria | Sinapis | Stellaria |
|---|---|---|---|---|
| 8 | 6 | 6 | 2 | 2 |
| 19 | 2 | 2 | 2 | 2 |
| 21 | 3 | 3 | 2 | 2 |
| 23 | 2 | 2 | 2 | 2 |
| 29 | 6 | 4 | 3 | 4 |
| 38 | 3 | 3 | 2 | 2 |
| 48 | 6 | 5 | 2 | 2 |
| 68 | 5 | 5 | 2 | 2 |
| 84 | 4 | 4 | 2 | 2 |
| 87 | 4 | 2 | 2 | 2 |
| 93 | 2 | 1 | 2 | 1 |
| 94 | 2 | 3 | 2 | 2 |
| 226 | 5 | 5 | 2 | 2 |
| 227 | 5 | 6 | 2 | 2 |
| 238* | 4 | 5 | 2 | 2 |
| 239* | 3 | 4 | 2 | 2 |
| 286 | 7 | 8 | 2 | 2 |
| 289* | 6 | 6 | 2 | 2 |
| 407 | 6 | 6 | 3 | 3 |

*Applied amount: 0.5 kg of active ingredient/hectare

EXAMPLE 5

Verification of selectivity on pre-emergence application

With the same test procedure as in Example 4, a number of varieties of plant seeds are treated with various applied amounts of active ingredient. The test results are evaluated according to the same scale of ratings.

| Pre-emergence action: | | | | |
|---|---|---|---|---|
| Action applied amount in kg of AS*/hectare | Comp. No. 23 | | Comp. No. 93 | |
| test plant | 0.125 | 0.06 | 0.125 | 0.06 |
| | 9 | 9 | 8 | 9 |
| Alopecurus myos | 2 | 3 | 2 | 2 |
| Echinochloa c.g. | 3 | 3 | 2 | 2 |
| Rottboellia ex. | 8 | 9 | 4 | 4 |
| Abutilon | 2 | 2 | 2 | 2 |
| Xanthium Sp. | 2 | 3 | 6 | 6 |
| Chenopodium Sp. | 3 | 3 | 2 | 2 |
| Ipomoea | 1 | 2 | 3 | 2 |
| Sinapis | 2 | 2 | 2 | 2 |
| Galium aparine | 2 | 2 | 1 | 1 |

-continued

Pre-emergence action:

| Action applied amount in kg of AS*/hectare test plant | Comp. No. 23 | | Comp. No. 93 | |
|---|---|---|---|---|
| | 0.125 | 0.06 | 0.125 | 0.06 |
| *Viola tricolor* | 3 | 4 | 2 | 2 |

* = active substance

EXAMPLE 6

Demonstration of the herbicidal activity after emergence of the plants (contact action)

A number of weeds and cultivated plants, both monocotyledons and dicotyledons, are sprayed in the 4- to 6-leaf stage with an aqueous active-ingredient dispersion in dosages of 4 kg of active substance per hectare, and then kept at 24° to 26° C. with 45–60% relative humidity. The test results are evaluated 15 days after the treatment, and an assessment made according to the same scale of ratings as in the pre-emergence test.

| | Post-emergence action Applied amount: 4 kg of active ingredient per hectare | | | | | | |
|---|---|---|---|---|---|---|---|
| Comp. No. | Avena | Set-aria | Lol-ium | Sol-anum | Sinapis | Stellaria | Phase-olus |
| 8 | 8 | 8 | 3 | 3 | 2 | 3 | 3 |
| 19 | 2 | 4 | 3 | 2 | 2 | 3 | 3 |
| 21 | 5 | 4 | 4 | 2 | 2 | 2 | 4 |
| 23 | 2 | 3 | 2 | 2 | 2 | 2 | 2 |
| 38 | 4 | 5 | 2 | 2 | 2 | 2 | 3 |
| 48 | 6 | 5 | 4 | 2 | 2 | 2 | 4 |
| 68 | 6 | 6 | 2 | 3 | 2 | 2 | 3 |
| 84 | 6 | 5 | 2 | 2 | 2 | 2 | 3 |
| 87 | 5 | 5 | 2 | 3 | 2 | 3 | 4 |
| 93 | 4 | 2 | 4 | 2 | 2 | 3 | 3 |
| 94 | 4 | 3 | 2 | 2 | 2 | 2 | 4 |
| 226 | 7 | 7 | 3 | 3 | 3 | 3 | 4 |
| 227 | 7 | 8 | 4 | 3 | 3 | 4 | 4 |
| 238* | 7 | 6 | 3 | 2 | 2 | 2 | 3 |
| 239* | 4 | 4 | 2 | 3 | 2 | 3 | 3 |
| 289* | 9 | 9 | 3 | 4 | 2 | 2 | 4 |

*Applied amount: 0.5 kg of active ingredient per hectare

EXAMPLE 7

Verification of selectivity with post-emergence application

With the same test procedure as in Example 6, a largish number of plants are treated with various applied amounts of active ingredient. The test results are evaluated according to the scale of ratings given in Example 4.

| | Post-emergence action | | | | | |
|---|---|---|---|---|---|---|
| Action applied amount in kg of AS/hectare test plants | Comp. No. 23 | | Comp. No. 38 | | Comp. No. 93 | |
| | 0.125 | 0.06 | 0.125 | 0.06 | 0.125 | 0.06 |
| wheat | 9 | 9 | 9 | 9 | 8 | 9 |
| maize | 3 | 3 | 4 | 5 | 9 | 9 |
| rice (dry) | 4 | 6 | 6 | 7 | 9 | 9 |
| *Alopecurus myos.* | 3 | 3 | 4 | 4 | 1 | 2 |
| *Cyperus escul.* | 9 | 9 | 3 | 3 | 4 | 9 |
| soya-bean | 2 | 2 | 6 | 6 | 9 | 9 |
| cotton | 4 | 4 | 7 | 7 | 9 | 9 |
| Sinapis | 2 | 3 | 2 | 2 | 1 | 1 |
| *Galium aparine* | 4 | 4 | 4 | 4 | 1 | 1 |
| *Viola tricolor* | 3 | 3 | 4 | 4 | 2 | 2 |

EXAMPLE 8

Verification of sprouting inhibition on stored potatoes

A number of commercially available potatoes of the "Urgenta" variety, exhibiting no germination (sprouting), are washed and dried. The potatoes are afterwards each immersed for one minute in active-ingredient emulsions of varying concentration; they are then laid out on filter paper in plastic dishes, and stored at temperatures of 14° and 21° C. in darkness with 50% relative humidity, and an evaluation is made 34 days after application. At the same time the loss in weight of the tubers and the weight of the sprouts, compared with those values in the case of the untreated control specimens are determined. The compounds according to the invention brought about in this test a complete prevention of sprouting. The loss in weight of the potatoes was less than 10% of that of the control potatoes.

EXAMPLE 9

Verification of the reduction in growth of tropical leguminous cover crops

The test plants (centrosema plumieri and centrosema pubescens) are cultivated up to the fully grown stage, and then cut back to a height of 60 cm. After 7 days, the active substance is sprayed on in the form of an aqueous emulsion. The test plants are maintained at 70% relative humidity and with 6000 lux of artificial light, 14 hours per day, at temperatures of 27° by day and 21° C. by night. The test results are assessed 4 weeks after application of the emulsion. The new growth occurring compared with that on the control plants is estimated and weighed, and the phytotoxicity is evaluated. The plants treated with the active ingredients of the formula I show in this test a clear reduction in new growth (less than 20% of the new growth occurring on untreated control plants), without the test plants having suffered damage.

EXAMPLE 10

Regulation of growth of soya-beans

Soya-beans of the variety "Hark" are sown in plastic containers holding a soil/peat/sand mixture in the ratio of 6:3:1, and are placed into a climatic chamber. By optimum choice of temperature, illumination, fertiliser addition and watering, the plants develop over about 5 weeks into the 5–6 trifoliate stage. At this point, the plants are sprayed until thoroughly dripping wet with the aqueous liquor of an active ingredient of the formula I, the active-ingredient concentration being up to 100 g of AS/hectare. An assessment of the results is made about 5 weeks after application of the active ingredient. The active ingredients of the formula I produce a marked increase in the number and in the weight of the pods on the leading shoots compared with the number and weight of pods on the untreated control plants.

What is claimed is:

1. An N-phenylsulfonyl-N'-pyrimidinyl- or -triazinylurea of the general formula I

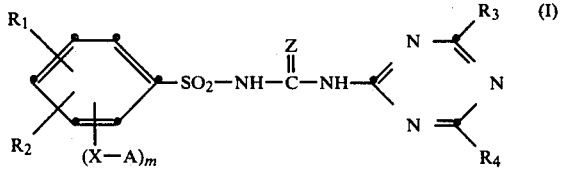

wherein
A is a $C_3$-$C_6$-alkynyl group,
X is oxygen, sulfur or a sulfinyl or sulfonyl bridge,
Z is oxygen or sulfur,
m is the number one or two,
$R_1$ is hydrogen, halogen, $C_1$-$C_5$-alkyl or $C_2$-$C_5$-alkenyl or a group —Y—$R_5$,
$R_2$ is hydrogen, halogen, $C_1$-$C_5$-alkyl, $C_2$-$C_5$-alkenyl or $C_1$-$C_4$-haloalkyl, or a group —Y—$R_5$, —COO$R_6$, —NO$_2$ or —CO—N$R_7$—$R_8$,
$R_3$ and $R_4$ independently of one another are hydrogen, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy, halogen or alkoxyalkyl having at most 4 carbon atoms,
$R_5$ and $R_6$ are each $C_1$-$C_5$-alkyl, $C_2$-$C_5$-alkenyl or $C_2$-$C_6$-alkynyl,
$R_7$ and $R_8$ independently of one another are each hydrogen, $C_1$-$C_5$-alkyl, $C_2$-$C_5$-alkenyl or $C_2$-$C_6$-alkynyl, and
Y is oxygen, sulfur or a sulfinyl or sulfonyl bridge;
and the salts of these compounds.

2. A compound according to claim 1, wherein Z is oxygen.

3. A compound according to claim 2, wherein one —X—A group is in the 2-position with respect to the sulfonyl group, and $R_3$ and $R_4$ together contain no more than 4 carbon atoms.

4. A compound according to claim 2, wherein one —X—A group is in each of the 2- and 5-positions with respect to the sulfonyl group, and $R_3$ and $R_4$ together contain no more than 4 carbon atoms.

5. A compound according to claim 3, wherein $R_1$ is hydrogen, and $R_2$ is in the 5- or 6-position with respect to the sulfonyl group.

6. A compound according to claim 5, wherein $R_2$ is hydrogen, and $R_3$ and $R_4$ are each $C_1$-$C_4$-alkyl, $C_1$-$C_4$-alkoxy, methylthio, 2,2,2-trifluoroethoxy, difluoromethoxy, 1,1,2,2-tetrafluoroethoxy, halogen or alkoxyalkyl.

7. A compound according to claim 6, wherein X is oxygen.

8. A compound according to claim 7, wherein A is propargyl.

9. A compound according to claim 1, wherein Z is sulfur, X is oxygen or sulfur, $R_3$ and $R_4$ independently of one another are each $C_1$-$C_3$-alkyl, $C_1$-$C_3$-alkoxy, $C_1$-$C_3$-alkylthio, difluoromethoxy or 2,2,2-trifluoroethoxy with together at most 4 carbon atoms, and A is —CH$_2$—C≡CH, —CH$_2$—C≡C—CH$_3$, —CH$_2$—CH$_2$—C≡CH, and the —X—A group occupies the 2-position, and m is the number 1.

10. N-(2-Propargyloxyphenylsulfonyl)-N'-(4-methoxy-6-methyl-1,3,5-triazin-2-yl)-urea according to claim 7.

11. N-(2-Propargyloxyphenylsulfonyl)-N'-(4-ethyl-6-methoxy-1,3,5-triazin-2-yl)-urea according to claim 7.

12. N-(2-Propargyloxyphenylsulfonyl)-N'-(4,6-dimethoxy-1,3,5-triazin-2-yl)-urea according to claim 7.

13. N-(2-Propargyloxyphenylsulfonyl)-N'-(4-ethoxy-6-methyl-1,3,5-triazin-2-yl)-urea according to claim 7.

14. A herbicidal and plant-growth-reducing composition which contains, as active ingredient, at least one N-phenylsulfonyl-N'-triazinyl-urea of the formula I, claim 1, together with carriers and/or other additives.

15. A method of controlling undesired plant growth, which method comprises applying thereto or to the locus thereof a herbicidally effective amount of a compound according to claim 1.

16. A method of suppressing plant growth, which method comprises applying thereto or to the locus thereof an effective amount of a compound according to claim 1.

17. A method of regulating plant growth of cultivated plants in the meaning of increasing the yield of the crops, which method comprises applying thereto or to the locus thereof an effective amount of a compound according to claim 1.

18. A method according to claim 15 for selectively controlling weeds in crops of cultivated plants, which method comprises applying the compound preemergence or postemergence.

19. A method according to claim 16 for suppressing plant growth beyond the two-leaf stage, which method comprises applying the compound preemergence.

20. A method according to claim 18 in cereals.

21. A method according to claim 17 in soybeans.

* * * * *